United States Patent [19]

MacNeil

[11] 4,031,711
[45] June 28, 1977

[54] COLD AIR BLAST WAKE-UP APPARATUS

[76] Inventor: Peter MacNeil, 3680 Mountain St., Montreal, Quebec, Canada

[22] Filed: May 24, 1976

[21] Appl. No.: 689,562

[52] U.S. Cl. .................................. 62/261; 98/89
[51] Int. Cl.² .................. F25D 23/12; E06B 7/02
[58] Field of Search ............... 62/201, 261; 98/89

[56] References Cited

UNITED STATES PATENTS

| 2,130,089 | 9/1938 | Hull | 98/89 |
|---|---|---|---|
| 2,461,432 | 2/1949 | Mitchell | 62/261 |
| 2,512,559 | 6/1950 | Williams | 62/261 |
| 2,566,865 | 9/1951 | Wingerter | 62/261 |
| 2,913,833 | 11/1959 | Glintz | 98/89 |
| 3,251,197 | 5/1966 | Dixon | 62/261 |

Primary Examiner—Lloyd L. King
Attorney, Agent, or Firm—Jack D. Slobod

[57] ABSTRACT

Wake-up apparatus includes an elongated hose having a funnel member at one end for coupling to the output side of a room air conditioner and a horizontally elongated rectangular outlet on the other end for placement on a mattress for directing air therealong. A rotatable damper vane mounted in the hose is controlled by a motor energized via an electric timer for driving the vane to an open position at a predetermined time for causing a blast of cold air along the mattress.

2 Claims, 5 Drawing Figures

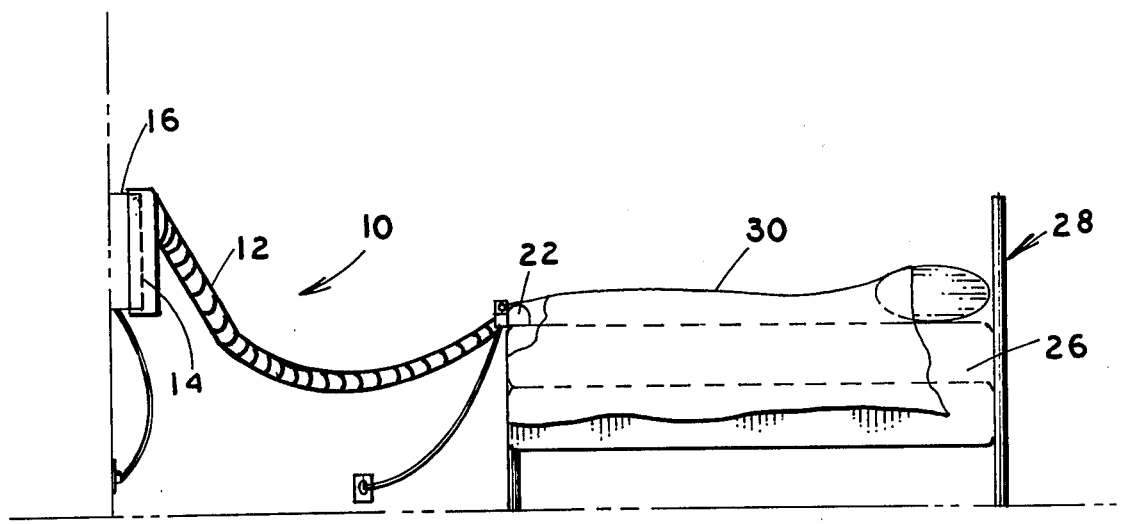
FIG. 1
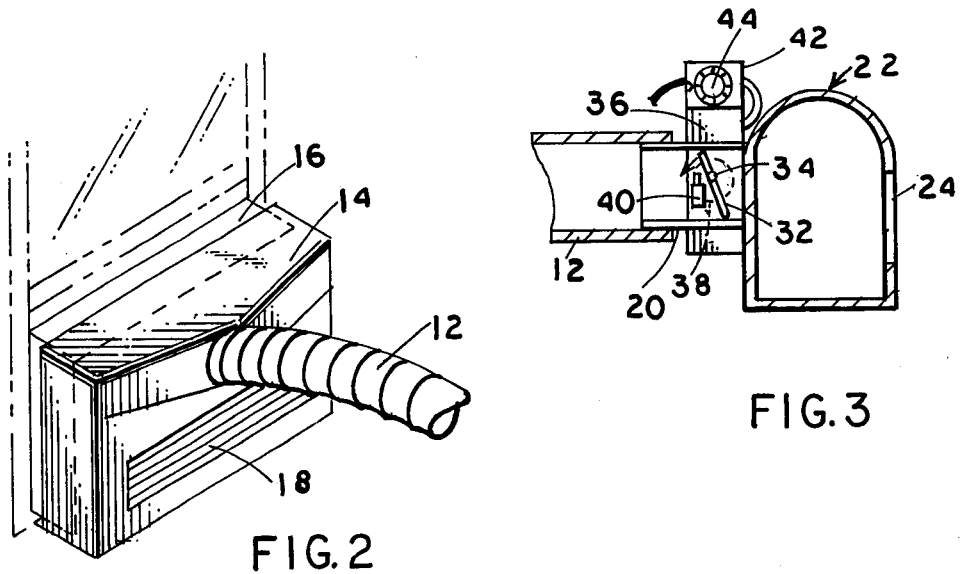
FIG. 2
FIG. 3
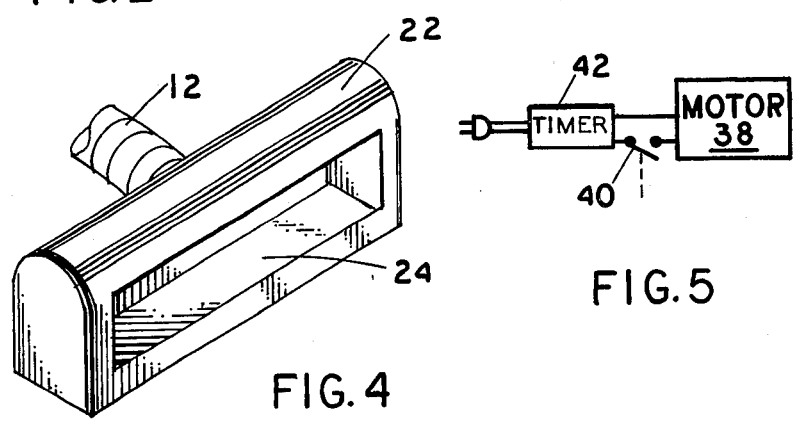
FIG. 4
FIG. 5

COLD AIR BLAST WAKE-UP APPARATUS

FIELD OF THE INVENTION

The present invention relates generally to apparatus for waking up a person from sleep at a predetermined time. In its particular aspects the present invention relates to a device for forming a blast of cold air across the top surface of a mattress at a predetermined time.

BACKGROUND OF THE INVENTION

Various devices have heretofore been used for waking up an individual from sleep at a predetermined time. Such devices as alarm clocks and clock radios have not proved adequately effective to awaken certain individuals having a low sensitivity to aural stimulus when sleeping. The problem is particularly acute in regard to the deaf.

While various blower systems have heretofore been proposed in conjunction with mattresses for promoting sleeping comfort, I am not aware of any prior proposal to utilize an automatic blast of cold air to awaken an individual from sleep at a predetermined time. Further, such mattress air blower systems, for example, U.S. Pat. No. 2,235,966 to Summers, are neither readily adaptable nor economically feasible for the purposes of the present invention because of their complexity.

OBJECTS OF THE INVENTION

It is an object of the present invention to provide a simple and inexpensive cold air blast wake-up device which operates in conjucntion with a conventional room air conditioner for conveying cold air therefrom and directing cold air flow across the top of a mattress at a predetermined time.

It is another object of the present invention to provide a cold air blast wake up device including an electrically controlled timer operated valve in series with a cold air duct leading to a mattress.

SUMMARY OF THE INVENTION

Briefly, the aforementioned and other objects of the present invention are satisfied by providing wake-up apparatus including an elongaged duct having coupling means at one end for attachement to the cold air outlet of a room air conditioner and having a horizontally elongated outlet on the other end configured for placement on a mattress for directing cold air therealong. An electrically controlled valve means in the duct has a normally closed position and an open position. Electrically timer means is coupled electrically thereto for opening said valve at a preset time to allow cold air from the outlet along the mattress.

The cold air provides a stimulus tending to awaken an individual from sleep and also make it rather uncomfortable to remain in bed.

Other objects, features and advantages of the present invention will become apparent upon perusal of the following detailed description of the preferred embodiment thereof when taken in conjunction with the appended drawing wherein:

FIG. 1 is an elevational view of the wake-up apparatus of the present invention in association with a bed and a room air conditioner;

FIG. 2 is an elevational pictorial presentation of the portion of the apparatus of FIG. 1 which is associated with the room air conditioner;

FIG. 3 is a cross-sectional side elevational view of the portion of the apparatus of FIG. 1 which is associated with the bed;

FIG. 4 is a pictorial presentation generally of the front of the apparatus portion in FIG. 3; and FIG. 5 is an electrical schematic for the apparatus portions in FIGS. 3 and 4.

DETAILED DESCRIPTION

Referring to FIGS. 1 through 5 of the drawing the wake-up apparatus of the present invention is generally indicated by the reference numeral 10. Apparatus 10 comprises an elongated flexible hose 12 carrying at one end a somewhat funnel-shaped member 14 of rectangular cross-section for engaging the outlet side of a window air conditioner 16. Member 14 serves as a coupling to the cold air outlet of air conditioner 16 and preferably includes a portion having a grating 18 for enabling some of the cold air output therefrom to escape to the room while the remainder is directed into hose 12.

The other end of hose 12 is fitted onto a tubular pipe 20 forming an input to a horizontally elongated box-like member 22 having a horizontally elongated rectangular output aperture 24 in a wall remote from pipe 20.

As shown in FIG. 1, member 22 is adapted to be placed on top of the mattress 26 of a bed 28. Preferably member 22 is positioned on the foot end of mattress 26 with its output aperture 24 facing the head end of the mattress. Also, preferably member 22 is positioned under the usual sheet or blanket 30 covering bed 28. It should be apparent that any air output from aperture 24 flows from the foot end to the head end of the bed between sheet 30 and mattress 26.

Within pipe 20 there is disposed a valve means including a rotatable damper vane 32 carried on a horizontal shaft 34 projecting into pipe 20 from a side thereof. A housing 36 alongside pipe 20 carries a motor 38 for driving shaft 34. The vane 32 is normally positioned generally vertically for blocking air flow through pipe 20. However, when motor 38 is electrically energized, shaft 34 is rotated counter clockwise as shown in FIG. 3 until the vane 32 is horizontally oriented. At that orientation the vane 32 strikes a normally closed limit switch 40 mounted in pipe 20. The switch 40 is in series with motor 38 for preventing further energization of the motor when the vane is horizontal.

The series combustion of motor 38 and limit switch 40 is energized from the output of a timer or time switch 42 having a dial 44 for setting the time of energization of its output.

In the operation of the apparatus 10, dial 44 is set for a predetermined time and when that time is reached motor 38 is energized to drive vane 32 to a horizontal orientation to enable cold air flow from the air conditioner 16 to exit aperture 24. This cold air, which is directed between mattress 26 and sheet 30 provides a stimulus to wake up an individual sleeping in bed 28.

While the preferred embodiment of the present invention has been described in specific detail, it should be understood that numerous modifications, additions and omissions in the details thereof are possible within the intended spirit and scope of the invention claimed herein.

What is claimed is:

1. Wake-up apparatus for use in conjunction with means for air conditioning a room including a cold air outlet into said room, and a mattress located in said room, said apparatus comprising: a flexible elongated duct; coupling means at one end of said duct for attachment to said cold air outlet for enabling cold air to be fed into said duct; outlet means on the other end of said duct configured to rest on said mattress, said outlet means having a horizontally elongated outlet aperture lying in a vertical plane when said outlet means rests on said mattress for directing said cold air in a steam along the top of said mattress; an electrically controlled valve means in series with said duct having open and closed alternative positions for selectively allowing or blocking air flow through said duct said valve means being normally in said closed position; and electrical timer means coupled to said valve means for placing said valve means in said open position at some preset time.

2. The apparatus of claim 1 wherein said coupling means includes a vent to said room and wherein said coupling means is configured for directing part of the cold air from said cold air outlet through said vent and part through said duct.

* * * * *